United States Patent
Yamamoto et al.

(10) Patent No.: US 7,582,592 B2
(45) Date of Patent: Sep. 1, 2009

(54) SKIN CLEANSING COMPOSITION COMPRISING A POLYOXYETHYLENE ALKYLETHER SULFATE, ETHER CARBOXYLIC ACID-TYPE SURFACTANT, ALKYL POLYGLYCOSIDE AND A HIGHER FATTY ACID OR HIGHER ALCOHOL

(75) Inventors: Naoko Yamamoto, Sumida-ku (JP); Masaki Shimizu, Sumida-ku (JP); Natsuko Toshida, Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 12/115,206

(22) Filed: May 5, 2008

(65) Prior Publication Data
US 2009/0023623 A1 Jan. 22, 2009

(30) Foreign Application Priority Data
May 14, 2007 (JP) .............................. 2007-127840

(51) Int. Cl.
*C11D 1/04* (2006.01)
*C11D 1/29* (2006.01)
*C11D 3/22* (2006.01)
*A61K 8/33* (2006.01)
*A61K 8/46* (2006.01)

(52) U.S. Cl. ................... 510/130; 510/153; 510/155; 510/156; 510/413; 510/414; 510/421; 510/424; 510/426; 510/437; 510/470; 510/474; 510/492; 510/535; 424/401; 424/70.13; 424/70.22; 424/70.31

(58) Field of Classification Search ................ 510/130, 510/153, 155, 156, 413, 414, 421, 424, 426, 510/437, 470, 474, 492, 535; 424/401, 70.13, 424/70.22, 70.31
See application file for complete search history.

(56) References Cited

U.S. PATENT DOCUMENTS 5,025,069 A * 6/1991 Deguchi et al. ............. 510/423

5,275,761 A 1/1994 Bergmann
2007/0269397 A1 * 11/2007 Terada ..................... 424/70.12

FOREIGN PATENT DOCUMENTS

| DE | 10 2005 062 830 | 1/2007 |
|---|---|---|
| EP | 0 236 677 | 9/1987 |
| EP | 0 374 702 | 6/1990 |
| EP | 1 428 499 | 6/2004 |
| JP | 2003-212733 | 7/2003 |
| JP | 2006-206443 | 8/2006 |
| WO | 98/02517 | 1/1998 |
| WO | 98/11871 | 3/1998 |
| WO | 2005/058260 | 6/2005 |

OTHER PUBLICATIONS

U.S. Appl. No. 12/115,206, filed May 5, 2008, Yamamoto et al.
U.S. Appl. No. 12/104,200, filed Apr. 16, 2008, Yamamoto et al.

* cited by examiner

*Primary Examiner*—Brian P Mruk
(74) *Attorney, Agent, or Firm*—Oblon, Spivak, McClelland, Maier & Neustadt, P.C.

(57) ABSTRACT

A skin cleansing composition contains, in addition to water, the following ingredients (A) to (D):
(A) a polyoxyethylene alkylether sulfate,
(B) an ether carboxylic acid-type surfactant,
(C) an alkyl polyglycoside, and
(D) one or more of a higher fatty acid and a higher alcohol.
A total amount of the ingredients (A), (B) and (C) ranges from 5 to 30 wt % based on the whole composition, with the ingredient (A) amounting to from 20 to 80 wt %, the ingredient (B) amounting to from 7 to 70 wt %, and the ingredient (C) amounting to from 7 to 70 wt %, the amount of the ingredient (D) ranges from 0.3 to 3 wt % based on the whole composition. A pH of the composition ranges from 4.5 to 7 when diluted to 5 wt % by weight with deionized water. The skin cleansing composition can produce abundant foam of fine and smooth quality without an increase in foam viscosity, and therefore, allows the body to be washed with comfort.

20 Claims, No Drawings

SKIN CLEANSING COMPOSITION COMPRISING A POLYOXYETHYLENE ALKYLETHER SULFATE, ETHER CARBOXYLIC ACID-TYPE SURFACTANT, ALKYL POLYGLYCOSIDE AND A HIGHER FATTY ACID OR HIGHER ALCOHOL

FIELD OF THE INVENTION

The present invention relates to a skin cleansing composition.

BACKGROUND OF THE INVENTION

Skin cleansing compositions are required to exhibit good lathering and to provide an excellent feeling in use. For example, JP-A-2006-206443 discloses that a skin cleansing composition, which contains a phosphate ester salt-type surfactant containing myristylphospholic acid ester salt, myristic acid or myristyl alcohol, and water and has a slightly acidic property, gives little skin irritation, shows good foamability, and produces fine, creamy and lubricious foam, and provides an excellent feeling in use. JP-A-2003-212733, on the other hand, discloses a hair cleansing composition, which contains an anionic surfactant having sulfuric acid residual groups, a higher alcohol having 10 to 14 carbon atoms and a cationic polymer, has good foamability and high-lubricity foam quality upon washing and smooth touch upon rinsing, and hence, is excellent feeling in use.

These cleansing compositions are, however, still not fully satisfactory in washing the body with comfort despite the availability of fine and creamy foam because, when washing the body with a cleansing means such as a nylon towel, foam can be hardly created from the nylon towel or the like.

Certain methods are known for the creation of fine foam, including the use of a long-chain surfactant and the addition of a liquid oil ingredient. These approaches make it possible to produce fine foam, but are still not fully satisfactory in washing the body with comfort because they lead to a reduction of foam volume.

SUMMARY OF THE INVENTION

The present invention provides a skin cleansing composition containing, in addition to water, the following ingredients (A) to (D):

(A) a polyoxyethylene alkyl ether sulfate,
(B) an ether carboxylic acid-type surfactant,
(C) an alkyl polyglycosides, and
(D) one or more of a higher fatty acid and a higher alcohol, wherein a total amount of the ingredients (A), (B) and (C) ranges from 5 to 30 wt % based on the whole composition, with the ingredient (A) amounting to from 20 to 80 wt %, the ingredient (B) amounting to from 7 to 70 wt %, and the ingredient (C) amounting to from 7 to 70 wt %, the amount of the ingredient (D) ranges from 0.3 to 3 wt % based on the whole composition, and a pH of the composition ranges from 4.5 to 7 when diluted to 5 wt % with deionized water.

The skin cleansing composition according to the present invention can produce abundant foam of fine and smooth quality without an increase in foam viscosity. When cleansing with a cleansing means, especially a nylon towel or nylon sponge widely used by consumers, it, therefore, makes it possible to readily create foam and to wash the body with comfort.

DETAILED DESCRIPTION OF THE INVENTION

The present invention relates to a skin cleansing composition, which can produce abundant foam of fine and smooth quality without an increase in foam viscosity and allows washing of the body with comfort.

The present inventors found that a skin cleansing composition equipped with the above-described properties can be obtained by choosing a specific combination of surfactants from surfactants for cleansing compositions and using them in combination with a higher fatty acid and/or a higher alcohol in specific proportions.

As the polyoxyethylene alkyl ether sulfate employed as the ingredient (A) in the present invention, one represented by the following formula is preferred.

wherein R represents an alkyl or alkenyl group having from 10 to 18 carbon atoms, n stands for a number of from 0.5 to 5 on average, and x represents a hydrogen atom, alkali metal, alkaline earth metal, ammonium or organic ammonium.

In the formula, an alkyl group having from 12 to 14 carbon atoms may be more preferred as R. The average number of moles of added ethylene oxide may range preferably from 0.5 to 5, with from 1 to 4 being more preferred.

As X, on the other hand, an alkali metal such as sodium or potassium; an alkaline earth metal such as calcium or magnesium; ammonium; an ammonium derived from an alkanolamine such as monoethanolamine, diethanolamine or triethanolamine; a cation derived from a basic amino acid such as arginine or lysine may be mentioned.

The ether carboxylic acid-type surfactant as the ingredient (B) is one of a class of compounds each containing a hydrophobic group and a carboxyl group via a polyoxyethylene chain or glycol ether unit. Examples include alkyl ether carboxylic acids or salts thereof, hydroxy ether carboxylic acids or salts thereof, and alkylamide ether carboxylic acids or salts thereof. Of these, alkylether carboxylic acids or salts thereof are preferred in terms of feeling in rinsing. They can be represented by the following structural formulas, respectively.

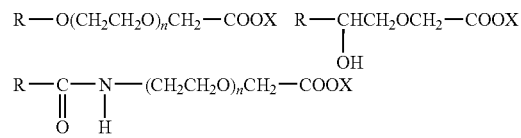

wherein R represents an alkyl or alkenyl group having from 10 to 18 carbon atoms, n stands for a number of from 0.5 to 10 on average, and x represents a hydrogen atom, alkali metal, alkaline earth metal, ammonium or organic ammonium.

In the formula, an alkyl group having from 12 to 16 carbon atoms may be more preferred as R. The average number n of moles of added ethylene oxide may range preferably from 0.5 to 10, with from 1 to 6 being more preferred.

As X, on the other hand, an alkali metal such as sodium or potassium; an alkaline earth metal such as calcium or magnesium; ammonium; an ammonium derived from an alkanolamine such as monoethanolamine, diethanolamine or triethanolamine; a cation derived from a basic amino acid such as arginine or lysine may be mentioned.

The alkyl polyglycosides as the ingredient (C) is a nonionic surfactant derived from a saccharide and a higher alcohol, and its examples include those represented by the following formula:

$$R-O(CH_2CH_2O)_m-Z_x$$

wherein R represents an alkyl group having from 8 to 20 carbon atoms, m stands for a number of from 0 to 10 on average, Z represents a saccharide residual group having 5 or 6 carbon atoms, and x stands for a number of from 1 to 5 on average.

In the above-described formula, R may more preferably be an alkyl group having from 9 to 15 carbon atoms, or a mixture of such alkyl groups. As Z, pentose or hexose is more preferred, with glucose being even more preferred. m may stand more preferably for a number of from 0 to 5 on average, and x may stand more preferably for a number of from 1 to 3 on average.

In the skin cleansing composition according to the present invention, a total content of the ingredients (A), (B) and (C) is from 5 to 30 wt %, with a range of from 10 to 20 wt % being preferred from the viewpoints of the fineness of foam and the ease of creation of foam from a nylon towel or the like.

The individual ingredients (A), (B) and (C) can be broken down preferably into the ingredient (A): from 20 to 80 wt %, the ingredient (B): from 7 to 70 wt % and the ingredient (C): from 7 to 70 wt %, all based on the total amount of the ingredients (A), (B) and (C). From the viewpoints of the volume of foam, the fineness of foam and the ease of creation of foam from a nylon towel or the like, their proportions may be more preferably the ingredient (A): from 45 to 70 wt %, the ingredient (B): from 7 to 50 wt % and the ingredient (C): from 7 to 50 wt %, even more preferably the ingredient (A): from 50 to 60 wt %, the ingredient (B): from 15 to 25 wt % and the ingredient (C): from 15 to 25 wt %.

Next, the higher fatty acid and/or higher alcohol as the ingredient (D) may be preferably those having from 10 to 18 carbon atoms, more preferably those having from 12 to 15 carbon atoms. It is even more preferred to use a higher fatty acid having from 10 to 18 carbon atoms and a higher alcohol having from 10 to 18 carbon atoms in combination. In such a case, the higher fatty acid and higher alcohol may be used at a weight ratio of preferably from 80:20 to 20:80, more preferably from 70:30 to 30:70 in that this weight ratio can produce fine foam and can avoid an increase in foam viscosity to permit easy creation of foam from a nylon towel or the like.

Even more preferably, lauric acid and myristyl alcohol may be used in combination.

As the ingredient (D), one or more of higher fatty acids and higher alcohols can be used. From the viewpoints of the volume and fineness of foam and the avoidance of an increase in foam viscosity to permit easy creation of foam from a nylon towel or the like, the ingredient (D) may be contained at preferably from 0.3 to 3 wt %, more preferably from 0.5 to 1.5 wt % in the whole composition.

The skin cleansing composition according to the present invention may further contain (E) an alkylglyceryl ether. The incorporation of this additional ingredient is preferred from the standpoint of foamability performance.

As the alkylglyceryl ether, monoglyceryl ether containing an alkyl or alkenyl group having from 4 to 12 carbon atoms is preferred, with a monoalkylglyceryl ether containing an alkyl group having from 6 to 10 carbon atoms being more preferred. Preferred alkyl groups include n-hexyl, n-octyl, 2-ethylhexyl, and n-decyl.

As the ingredient (E), one or more alkylglyceryl ethers can be used. The ingredient (E) may be contained at preferably from 0.25 to 3 wt %, more preferably from 0.5 to 1.5 wt % in the whole composition.

In addition to the above-described ingredients, the skin cleansing composition according to the present invention may also contain other surfactants employed in a usual cleansing composition. Specific examples include an anionic surfactant such as alkylbenzenesulfonate, α-olefinsulfonate, alkanesulfonate, α-sulfo fatty acid ester salt, a monoalkyl phosphate ester salt and acyl-L-glutamate; a nonionic surfactant such as polyoxyalkylene alkyl ether, fatty acid mono- or di-alkanolamide, polyoxyalkylene block polymer, glycerin fatty acid ester; a cationic surfactant such as a quaternary ammonium salt; and an amphoteric surfactant such as carbobetaine, sulfobetaine, imidazolinium betaine, hydroxybetaine and fatty acid amidobetaine.

The skin cleansing composition according to the present invention may further contain various ingredients, which are commonly employed in cleansing compositions, as needed. It is possible to contain, for example, a humectant such as propylene glycol, dipropylene glycol, glycerin and sorbitol; a viscosity adjuster such as methylcellulose, polyoxyethylene glycol distearate; an antimicrobial agent such as triclosan and trichlorcarban; an anti-inflammatory such as potassium glycyrrhizinate and tocopherol acetate; a preservative such as methylparaben, butylparaben, phenoxyethanol and benzoate salts; and in addition, a colorant, a fragrance, an ultra violet absorber, an antioxidant and the like, as needed.

The skin cleansing composition according to the present invention can be produced in a manner known per se in the art by weighing the ingredients and mixing them in a desired order in water or an aqueous medium composed mainly of water and containing another water-soluble solvent such as an alcohol. It can be applied as a body shampoo, facial wash, hand soap, cleansing preparation or the like.

The skin cleansing composition according to the present invention has a pH of from 4.5 to 7, preferably a pH of from 4.5 to 6.5 when diluted to 5 wt % with deionized water. The adjustment to a pH in such a range is preferred, because the thus pH-adjusted skin cleansing composition is good in lathering, foam volume and foam quality and gives little skin irritation during cleansing.

The pH of the skin cleansing composition can be adjusted, as needed, with a pH adjuster such as an inorganic acid such as hydrochloric acid, sulfuric acid or phosphoric acid; an organic acid such as citric acid, succinic acid, lactic acid, malic acid, pyrrolidonecarboxylic acid, tartaric acid or glycolic acid; an acidic amino acid such as glutamic acid or aspartic acid; a hydroxide such as sodium hydroxide or potassium hydroxide; ammonia or aqueous ammonia; or a basic amino acid such as arginine or lysine.

From the standpoint of lathering performance, the skin cleansing composition according to the present invention may preferably be in a liquid form having a viscosity of not higher than 20,000 mPa·s, desirably not higher than 8,000 mPa·s at 25° C. In the present invention, the above-described viscosity can be measured using a vibro-viscometer (manufactured by A & D Co., Ltd.; Model: "CVJ5000", trade name).

The following examples further describe and demonstrate embodiments of the present invention. The examples are given solely for the purpose of illustration and are not to be construed as limitations of the present invention.

EXAMPLES

Examples 1-20 & Comparative Examples 1-9

Skin cleansing compositions of the formulas shown in Table 1 to Table 4 were produced. With respect to the skin cleansing compositions obtained, the pHs of these 5 wt % aqueous solutions were measured. Further, they were assessed for foam volume, foam fineness, the ease of creation of foam from a nylon towel and cleansing comfort. The results are also shown in Table 1 to Table 4.

(Production Procedure)

In each example or comparative example, the ingredients shown in the corresponding table were weighed and added into deionized water, followed by thorough stirring at 50° C. to afford the skin cleansing composition. Sodium hydroxide or malic acid was added as much as needed to adjust the pH of its 20-fold dilution so as to be slightly acidic.

(Assessment Methods)

(1) pH:

The pH of each composition was measured at 25° C. using a pH meter (manufactured by Horiba, Ltd.; Model No.: "F-22", trade name) after the composition was diluted to 20-fold with deionized water to obtain a 5 wt % aqueous solution.

(2) The Volume of Foam

Each composition was diluted with hard water (hardness: 4 mg/L) to 150-fold to provide a sample. The sample (7.5 mL) was placed in a graduated 50-mL glass cylinder equipped with a stopper cock, and the stopper cock was placed thereon. Using a shaker (manufactured by Iwaki Sangyo K.K.; Model No.: "UNIVERSAL SHAKER V-SX", trade name), the cylinder was shaken for 30 seconds at a rate of 300 strokes/min, and immediately after the completion of the shaking, the volume of foam was read. The measurement results were ranked in accordance with the following assessment standards.

5: 4.5 cm≦height of foam
4: 3.5 cm≦height of foam <4.5 cm
3: 2.5 cm≦height of foam <3.5 cm
2: 1.5 cm≦height of foam <2.5 cm
1: height of foam <1.5 cm (3) Fineness of Foam Each composition was diluted with hard water (hardness: 4 mg/L) to 10-fold to provide a sample. The sample (7.5 mL) was placed in a graduated 50-mL glass cylinder equipped with a stopper cock, and the stopper cock was placed thereon. Using the shaker (manufactured by Iwaki Sangyo K.K.; Model No.: "UNIVERSAL SHAKER V-SX", trade name), the cylinder was shaken for 30 seconds at a rate of 300 strokes/min, and immediately after the completion of the shaking, an image of the sample was captured (×50 magnification) by DSA (manufactured by Keyence Corporation; digital microscope; Model No.: "VHX-100", trade name). The particle sizes of 20 foam bubbles were measured, and their average was recorded as an average bubble size. The measurement results were ranked in accordance with the following assessment standards.

5: average bubble size of foam <800 μm
4: 800 μm≦average bubble size of foam <1,100 μm
3: 1,100 μm≦average bubble size of foam <1,400 μm
2: 1,400 μm≦average bubble size of foam <1,800 μm
1: 1,800 μm≦average bubble size of foam (4) Ease of Creation of Foam from Nylon Towel Each composition (3 mL) was dispensed on a nylon towel which had been soaked with tap water. After the towel was rubbed against itself five times, an observation was made as to how foam was created. It is to be noted that the towel used in the above assessment was "WATER COLOR NYLON (REGULAR TEXTURE)" (trade name; nylon 100%; size: 27 cm×105 cm); product of Marna Cosmetics Co., Ltd.).

A: Foam was created in a large volume from nylon towel.
B: Foam was created in a rather large volume from nylon towel.
C: Foam was created in a rather small volume from nylon towel.
D: Foam was created in a small volume from nylon towel.

(5) Cleansing Comfort

Using each composition, ten (10) expert assessors cleansed the body once a day. The cleansing was conducted for 3 consecutive days, and an assessment was performed as to whether or not the assessors were able to wash the body with comfort.

The results determined based on the overall assessment over the 3 days were indicated in accordance with the following standards. It is to be noted that the term "comfort" means that, when a skin cleansing composition is lathered with a nylon towel, foam is promptly created and the body is covered with foam sufficient to wash the body from the beginning to the end.

A: number of assessors replied "the body was washable with comfort": ≧8
B: number of assessors replied "the body was washable with comfort": 5 to 7
C: number of assessors replied "the body was washable with comfort": 2 to 4
D: number of assessors replied "the body was washable with comfort": 0 or 1

TABLE 1

|   | Ingredients (wt %) | Examples 1 | 2 | 3 | 4 | 5 | 6 | 7 | 8 |
|---|---|---|---|---|---|---|---|---|---|
| A | Sodium polyoxyethylene(2) laurylether sulfate | 7.5 | 12.0 | 12.0 | 10.0 | 10.0 | 8.5 | 6.8 | 6.8 |
| B | Polyoxyethylene(4.5) laurylether Carboxylate | 3.8 | 1.0 | 2.0 | 2.0 | 3.0 | 3.7 | 1.5 | 6.8 |
|   | Potassium monoalkylphosphate |   |   |   |   |   |   |   |   |
| C | Alkyl(C9-C13) glycoside | 3.8 | 2.0 | 1.0 | 3.0 | 2.0 | 2.9 | 6.8 | 1.5 |
| D | Lauric acid | 0.5 | 0.5 | 0.5 | 0.5 | 0.5 | 0.5 | 0.5 | 0.5 |
|   | Myristyl alcohol | 0.5 | 0.5 | 0.5 | 0.5 | 0.5 | 0.5 | 0.5 | 0.5 |
|   | Dipropylene glycol | 3.0 | 3.0 | 3.0 | 3.0 | 3.0 | 3.0 | 3.0 | 3.0 |
|   | Lauramidopropyl betaine | 2.5 | 2.5 | 2.5 | 2.5 | 2.5 | 2.5 | 2.5 | 2.5 |
|   | Laurylhydroxysulfobetaine |   |   |   |   |   |   |   |   |

TABLE 1-continued

|   | Ingredients (wt %) | Examples 1 | 2 | 3 | 4 | 5 | 6 | 7 | 8 |
|---|---|---|---|---|---|---|---|---|---|
| E | 2-Ethylhexyl glyceryl ether | 1.5 | 1.5 | 1.5 | 1.5 | 1.5 | 1.5 | 1.5 | 1.5 |
|   | Dimethyldiallylammonium chloride-acrylamide (50:50) copolymer (9%) | 0.2 | 0.2 | 0.2 | 0.2 | 0.2 | 0.2 | 0.2 | 0.2 |
|   | Sodium hydroxide(48%) | 0.45 | 0.12 | 0.24 | 0.24 | 0.35 | 0.44 | 0.18 | 0.8 |
|   | Deionized water | Balance | Balance | Balance | Balance | Balance | Balance | Balance | Balance |
|   | Total | 100 | 100 | 100 | 100 | 100 | 100 | 100 | 100 |
|   | (A) + (B) + (C) | 15 | 15 | 15 | 15 | 15 | 15 | 15 | 15 |
|   | (A):(B):(C) | 50:25:25 | 80:7:13 | 80:13:7 | 67:13:20 | 67:20:13 | 56:25:19 | 45:10:45 | 45:45:10 |
|   | pH (5 wt %) | 6.2 | 6.1 | 6.3 | 6.0 | 6.4 | 6.2 | 6.1 | 6.3 |
|   | Foam volume | 5 | 4 | 4 | 5 | 5 | 5 | 5 | 5 |
|   | Foam fineness | 4 | 4 | 4 | 4 | 4 | 4 | 4 | 4 |
|   | Ease of foam creation from nylon towel | A | B | B | B | B | A | B | B |
|   | Cleansing comfort | A | B | B | A | A | A | A | A |

TABLE 2

|   | Ingredients (wt %) | Examples 9 | 10 | 11 | 12 | 13 | 14 | Comparative Examples 1 | 2 |
|---|---|---|---|---|---|---|---|---|---|
| A | Sodium polyoxyethylene(2) laurylether sulfate | 3.0 | 3.0 | 3.0 | 7.5 | 7.5 | 7.5 | 15.0 |  |
| B | Polyoxyethylene(4.5) laurylether carboxylate | 2.0 | 10.0 | 6.0 | 3.8 | 3.8 | 3.8 |  | 15.0 |
|   | Potassium monoalkylphosphate |  |  |  |  |  |  |  |  |
| C | Alkyl(C9-C13) glycoside | 10.0 | 2.0 | 6.0 | 3.8 | 3.8 | 3.8 |  |  |
| D | Lauric acid | 0.5 | 0.5 | 0.5 | 0.5 | 0.5 | 0.5 | 0.5 | 0.5 |
|   | Myristyl alcohol | 0.5 | 0.5 | 0.5 | 0.5 | 0.5 | 0.5 | 0.5 | 0.5 |
|   | Dipropylene glycol | 3.0 | 3.0 | 3.0 | 3.0 | 3.0 | 3.0 | 3.0 | 3.0 |
|   | Lauramidopropyl betaine | 2.5 | 2.5 | 2.5 |  |  | 2.5 | 2.5 | 2.5 |
|   | Laurylhydroxysulfobetaine |  |  |  | 2.5 |  |  |  |  |
| E | 2-Ethylhexyl glyceryl ether | 1.5 | 1.5 | 1.5 | 1.5 | 1.5 |  | 1.5 | 1.5 |
|   | Dimethyldiallylammonium chloride-acrylamide (50:50) copolymer (9%) | 0.2 | 0.2 | 0.2 | 0.2 |  | 0.2 | 0.2 | 0.2 |
|   | Sodium hydroxide(48%) | 0.24 | 1.2 | 0.72 | 0.45 | 0.45 | 0.45 |  |  |
|   | Deionized water | Balance | Balance | Balance | Balance | Balance | Balance | Balance | Balance |
|   | Total | 100 | 100 | 100 | 100 | 100 | 100 | 100 | 100 |
|   | (A) + (B) + (C) | 15 | 15 | 15 | 15 | 15 | 15 | — | — |
|   | (A):(B):(C) | 20:13:67 | 20:67:13 | 20:40:40 | 50:25:25 | 50:25:25 | 50:25:25 | 100:0:0 | 0:100:0 |
|   | pH (5 wt %) | 6.0 | 5.8 | 6.3 | 6.0 | 6.4 | 5.8 | 5.6 | 5.9 |
|   | Foam volume | 4 | 4 | 4 | 4 | 3 | 4 | 1 | 1 |
|   | Foam fineness | 3 | 4 | 4 | 4 | 4 | 4 | 3 | 4 |
|   | Ease of foam creation from nylon towel | B | B | B | A | B | B | D | D |
|   | Cleansing comfort | B | B | B | A | B | A | D | D |

TABLE 3

|   | Ingredients (wt %) | Comparative Examples 3 | 4 | 5 | 6 | 7 | 8 |
|---|---|---|---|---|---|---|---|
| A | Sodium polyoxyethylene(2) laurylether sulfate |  | 10.0 | 10.0 |  | 1.5 |  |
| B | Polyoxyethylene(4.5) laurylether carboxylate |  |  | 5.0 | 7.5 | 6.8 | 3.8 |
|   | Potassium monoalkylphosphate |  |  |  |  |  | 7.5 |
| C | Alkyl(C9-C13) glycoside | 15.0 | 5.0 |  | 7.5 | 6.8 | 3.8 |
| D | Lauric acid | 0.5 | 0.5 | 0.5 | 0.5 | 0.5 | 0.5 |
|   | Myristyl alcohol | 0.5 | 0.5 | 0.5 | 0.5 | 0.5 | 0.5 |
|   | Dipropylene glycol | 3.0 | 3.0 | 3.0 | 3.0 | 3.0 | 3.0 |
|   | Lauramidopropyl betaine | 2.5 | 2.5 | 2.5 | 2.5 | 2.5 | 2.5 |
|   | Laurylhydroxysulfobetaine |  |  |  |  |  |  |
| E | 2-Ethylhexyl glyceryl ether | 1.5 | 1.5 | 1.5 | 1.5 | 1.5 | 1.5 |
|   | Dimethyldiallylammonium chloride-acrylamide (50:50) copolymer (9%) | 0.2 | 0.2 | 0.2 | 0.2 | 0.2 | 0.2 |
|   | Sodium hydroxide(48%) |  |  | 0.6 | 0.9 | 0.8 | 0.45 |

TABLE 3-continued

| | Comparative Examples | | | | | |
|---|---|---|---|---|---|---|
| Ingredients (wt %) | 3 | 4 | 5 | 6 | 7 | 8 |
| Deionized water | Balance | Balance | Balance | Balance | Balance | Balance |
| Total | 100 | 100 | 100 | 100 | 100 | 100 |
| (A) + (B) + (C) | — | — | — | — | 15 | — |
| (A):(B):(C) | 0:0:100 | 67:0:33 | 67:33:0 | 0:50:50 | 10:45:45 | — |
| pH (5 wt %) | 6.0 | 6.3 | 5.7 | 5.9 | 6.3 | 6.2 |
| Foam volume | 4 | 4 | 1 | 2 | 3 | 1 |
| Foam fineness | 2 | 3 | 3 | 4 | 4 | 2 |
| Ease of foam creation from nylon towel | C | C | D | D | C | D |
| Cleansing comfort | D | C | D | D | C | D |

TABLE 4

| | | Examples | | | | | | Comp. Example |
|---|---|---|---|---|---|---|---|---|
| | Ingredients (wt %) | 15 | 16 | 17 | 18 | 19 | 20 | 9 |
| A | Sodium polyoxyethylene (2) laurylether sulfate | 7.5 | 7.5 | 7.5 | 7.5 | 7.5 | 7.5 | 7.5 |
| B | Polyoxyethylene (4.5) laurylether carboxylate | 3.8 | 3.8 | 3.8 | 3.8 | 3.8 | 3.8 | 3.8 |
| C | Alkyl(C9-C13) glycoside | 3.8 | 3.8 | 3.8 | 3.8 | 3.8 | 3.8 | 3.8 |
| D | Lauric acid | 1.0 | 1.0 | | | 0.8 | | |
| | Myristic acid | | | 1.0 | | | 0.6 | |
| | Palmitic acid | | | | | | 0.3 | |
| | Stearic acid | | | | | | 0.1 | |
| | Myristyl alcohol | 1.0 | | | 1.0 | 0.2 | | |
| | Dipropylene glycol | 3.0 | 3.0 | 3.0 | 3.0 | 3.0 | 3.0 | 3.0 |
| | Lauramidopropyl betaine | 2.5 | 2.5 | 2.5 | 2.5 | 2.5 | 2.5 | 2.5 |
| E | 2-Ethylhexyl glyceryl ether | 1.5 | 1.5 | 1.5 | 1.5 | 1.5 | 1.5 | 1.5 |
| | Dimethyldiallylammonium chloride-acrylamide (50:50) copolymer (9%) | 0.2 | 0.2 | 0.2 | 0.2 | 0.2 | 0.2 | 0.2 |
| | Sodium hydroxide(48%) | 0.45 | 0.45 | 0.45 | 0.45 | 0.45 | 0.45 | 0.45 |
| | Deionized water | Balance | Balance | Balance | Balance | Balance | Balance | Balance |
| | Total | 100 | 100 | 100 | 100 | 100 | 100 | 100 |
| | (A) + (B) + (C) | 15 | 15 | 15 | 15 | 15 | 15 | 15 |
| | (A):(B):(C) | 50:25:25 | 50:25:25 | 50:25:25 | 50:25:25 | 50:25:25 | 50:25:25 | 50:25:25 |
| | pH (5 wt %) | 6.4 | 6.0 | 6.1 | 6.0 | 5.9 | 6.3 | 6.1 |
| | Foam volume | 3 | 3 | 4 | 3 | 4 | 5 | 1 |
| | Foam fineness | 4 | 3 | 4 | 3 | 4 | 4 | 1 |
| | Ease of foam creation from nylon towel | B | A | B | A | A | B | D |
| | Cleansing comfort | B | B | B | B | A | A | D |

The invention claimed is:

1. A skin cleansing composition comprising, in addition to water, the following ingredients (A) to (D):
   (A) a polyoxyethylene alkylether sulfate,
   (B) a surfactant which comprises a hydrophobic group and a carboxyl group via a polyoxyethylene chain or glycol ether unit,
   (C) an alkyl polyglycoside, and
   (D) one or more of a higher fatty acid and a higher alcohol,
   wherein a total amount of the ingredients (A), (B) and (C) ranges from 5 to 30 wt % based on the whole composition, with the ingredient (A) amounting to from 20 to 80 wt %, the ingredient (B) amounting to from 7 to 70 wt %, and the ingredient (C) amounting to from 7 to 70 wt %, the amount of the ingredient (D) ranges from 0.3 to 3 wt % based on the whole composition, and a pH of the composition ranges from 4.5 to 7 when diluted to 5 wt % with deionized water.

2. The skin cleansing composition according to claim 1, wherein the ingredient (D) comprises a higher fatty acid having from 10 to 18 carbon atoms and a higher alcohol having from 10 to 18 carbon atoms at a weight ratio of from 80:20 to 20:80.

3. The skin cleansing composition according to claim 1, further comprising an alkylglyceryl ether as an ingredient (E).

4. The skin cleansing composition according to claim 2, further comprising an alkylglyceryl ether as an ingredient (E).

5. The skin cleansing composition according to claim 1, wherein ingredient (A) has the formula

wherein R represents an alkyl or alkenyl group having from 10 to 18 carbon atoms, n stands for a number of from 0.5 to 5 on average, and X represents a hydrogen atom, alkali metal, alkaline earth metal, ammonium or organic ammonium.

6. The skin cleansing composition according to claim 5, wherein R is an alkyl group having from 12 to 14 carbon atoms and n is from 1 to 4.

7. The skin cleansing composition according to claim 1, wherein ingredient (B) has one of the following formulae:

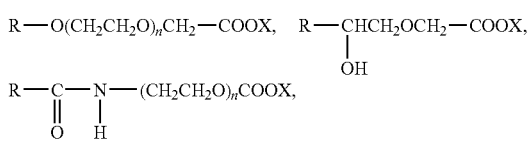

wherein R represents an alkyl or alkenyl group having from 10 to 18 carbon atoms, n stands for a number of from 0.5 to 10 on average, and X represents a hydrogen atom, alkali metal, alkaline earth metal, ammonium or organic ammonium.

8. The skin cleansing composition according to claim 7, wherein R is an alkyl group having from 12 to 16 carbon atoms and n is from 1 to 6.

9. The skin cleansing composition according to claim 1, wherein ingredient (C) is represented by the formula R—O(CH$_2$CH$_2$O)$_m$-Z$_x$ wherein R represents an alkyl group having from 8 to 20 carbon atoms, m stands for a number of from 0 to 10 on average, Z represents a saccharide residual group having 5 or 6 carbon atoms, and x stands for a number of from 1 to 5 on average.

10. The skin cleansing composition according to claim 9, wherein R is an alkyl group of from 9 to 15 carbon atoms or a mixture thereof; Z is pentose, hexose or glucose; m is from 0 to 5 on average, and x is from 1 to 3 on average.

11. The skin cleansing composition according to claim 10, wherein Z is glucose.

12. The skin cleansing composition according to claim 1, wherein the total content of the ingredients (A), (B) and (C) is from 10 to 20 wt %.

13. The skin cleansing composition according to claim 1, wherein based on the total amount of ingredients (A), (B) and (C), ingredient (A) is present in an amount of 45 to 70 wt %, ingredient (B) is present in an amount of from 7 to 50 wt %, and ingredient (C) is present in an amount of 7 to 50%.

14. The skin cleansing composition according to claim 13, wherein ingredient (A) is present in an amount of 50 to 60 wt %, ingredient (B) is present in an amount of from 15 to 25 wt %, and the amount of ingredient (C) is present in an amount of from 15 to 25 wt %.

15. The skin cleansing composition according to claim 2, wherein the number of carbon atoms is from 10 to 15 carbon atoms and the weight ratio is from 70:30 to 30:70.

16. The skin cleansing composition according to claim 1, wherein ingredient (D) is present in an amount of 0.5 to 1.5 wt %.

17. The skin cleansing composition according to claim 3, wherein ingredient (E) is a monoglyceryl ether containing an alkyl or alkenyl group having from 4 to 12 carbon atoms.

18. The skin cleansing composition according to claim 1, wherein ingredient (E) is present in an amount of 0.25 to 3 wt %.

19. The skin cleansing composition according to claim 1, wherein said pH ranges from 4.5 to 6.5.

20. A method comprising cleansing the skin with the skin cleansing composition according to claim 1.

* * * * *